US 9,808,621 B2

(12) United States Patent
Kelly

(10) Patent No.: US 9,808,621 B2
(45) Date of Patent: Nov. 7, 2017

(54) SYSTEM AND METHOD FOR REVERSING THE EFFECTS OF PARALYSIS

(71) Applicant: Laura Kelly, Topanga, CA (US)

(72) Inventor: Laura Kelly, Topanga, CA (US)

( * ) Notice: Subject to any disclaimer, the term of this patent is extended or adjusted under 35 U.S.C. 154(b) by 0 days.

(21) Appl. No.: 14/818,933

(22) Filed: Aug. 5, 2015

(65) Prior Publication Data
US 2017/0036022 A1    Feb. 9, 2017

(51) Int. Cl.
*A61N 1/36* (2006.01)
*A61B 5/0478* (2006.01)
*A61N 1/05* (2006.01)

(52) U.S. Cl.
CPC ........ *A61N 1/36017* (2013.01); *A61B 5/0478* (2013.01); *A61N 1/0502* (2013.01)

(58) Field of Classification Search
None
See application file for complete search history.

(56) References Cited

U.S. PATENT DOCUMENTS

| 3,572,699 | A * | 3/1971 | Nies | A61B 5/221 482/5 |
| 2007/0142874 | A1 * | 6/2007 | John | A61N 1/3605 607/45 |
| 2011/0224682 | A1 * | 9/2011 | Westlund | A61B 17/3468 606/129 |
| 2012/0238920 | A1 * | 9/2012 | Schnapp | A61H 1/0285 601/5 |
| 2014/0094721 | A1 * | 4/2014 | Diallo | A61H 1/024 601/5 |
| 2014/0296752 | A1 | 10/2014 | Edgerton et al. | |

OTHER PUBLICATIONS

Geng X, Sun T, Li JH, Zhao N, Wang Y, Yu HL. Electroacupuncture in the repair of spinal cord injury: inhibiting the Notch signaling pathway and promoting neural stem cell proliferation. Neural Regen Res. Mar. 2015;10(3):394-403.*
Naeser, Acupuncture in the Treatment of Paralysis Due to Central Nervous System Damage, The Journal of Alternative and Complementary Medicine, vol. 2, No. 1, pp. 211-248.

(Continued)

*Primary Examiner* — Brian T Gedeon
*Assistant Examiner* — Ankit D Tejani
(74) *Attorney, Agent, or Firm* — William J. Benman; Benman, Brown & Williams

(57) ABSTRACT

A method and system for applying therapeutic stimulation to a patient stricken with paralysis or other condition. The inventive method includes the steps of: inserting an acupuncture needle against the spine of the patient and applying an electrical potential to the needle with a signal that mimics natural neural impulses in the body. The needle is located depending on the nature of the patient's condition. In the illustrative application, the needle is inserted against the ligamentum flavum of the patient's spine at L3. In the best mode, the patient's legs are moved during the application of the electrical potential. The inventive system is adapted to minimize a notch reaction and includes an electrode inserted into a tissue of the patient and a circuit for applying an electrical potential to the electrodes with a signal that mimics natural neural impulses in the body.

14 Claims, 5 Drawing Sheets

(56) References Cited

OTHER PUBLICATIONS

Harkema et al., Effect of Epidural Stimulation of the Lumbosacral Spinal Cord on Voluntary Movement, Standing, and Assisted Stepping After Motor Complete Paraplegia: A Case Study, Published online May 20, 2011 DOI:10.1016/S0140-6736(11)60711-3; www.thelancet.com.

Inoue et al., Direct Current Electrical Stimulation of Acupuncture Needles for Peripheral Nerve Regeneration: An Exploratory Case Series, Acupunct Med 2011;29:88-93. doi:10.1136/aim.2010.003046.

Gerasimenko et al., Transcutaneous Electrical Spinal-Cord Stimulation in Humans, Annals of Physical and Rehabilitation Medicine, (2015), http://dx.doi.org/10.1016/j.rehab.2015.05.003.

* cited by examiner

SYSTEM AND METHOD FOR REVERSING THE EFFECTS OF PARALYSIS

BACKGROUND OF THE INVENTION

Field of the Invention

The present invention relates to electrical and electronic circuits and systems. More specifically, the present invention relates to electrical and electronic circuits and systems for providing electrical stimulation therapy.

Description of the Related Art

According to a study initiated by the Christopher & Dana Reeve Foundation, nearly 1 in 50 people in the U.S. are living with paralysis. Paralysis is a loss of muscle function in one or more muscle. The principal methods for treating paralysis typically include surgery, use of a brace, anti-inflammatories and/or pain medication, and confinement to a bed.

The potential of acupuncture in the restoration of motor control in cases of paralysis has been established. In a seminal meta-analysis work, Naeser devised a scale that included categories of "improved," "markedly effective," "essentially cured" and "cured." (See *Acupuncture in the Treatment of Paralysis Due To Central Nervous System Damage* by Naeser M. A., published in J Altern Complem Med. 2 (1): 211-248.) Across a number of studies of paralysis due to head injury where acupuncture treatments were applied, the author reported 83.2% of cases at the markedly effective level or better.

With the introduction of electro-acupuncture additional potential has been recognized. In a study of seven patients with peripheral nerve damage, Inoue et al. applied direct current electroacupuncture proximal to the site of injury and reported levels of improvement in cases of paralysis due to neurapraxia and axonotmesis. (See *Direct Current Electrical Stimulation Of Acupuncture Needles For Peripheral Nerve Regeneration: An Exploratory Case Series* by Inoue M, Katsumi Y, Itoi M, Hojo T, Nakajima M, Ohashi S, Oi Y, Kitakoji H. published in Acupunct Med. 2011, 29 (2): 88-93.) Ding et al showed that electroacupuncture promotes survival and differentiation of bone marrow mesenchymal stem cells and functional improvement in spinal cord-transected rats, and Huang et al showed that electroacupuncture promotes an increase in oligodendrocytes and myelination and functional recovery in the demyelinated spinal cord. Additionally, the success of the NIH/Reeves study confirms that electrical stimulation can indeed influence paralytic states. (See *Bone Marrow Mesenchymal Stem Cells And Electroacupuncture Downregulate The Inhibitor Molecules and Promote The Axonal Regeneration In The Transected Spinal Cord Of Rats*, by Ding Y., Yan Q., Ruan J. W., Zhang Y. Q., Li W. J., Zeng X, Huang S. F., Zhang Y. J., Wang S., Dong H., Zeng Y. S., published in Cell Transplant, 2011; 20:475-491. [PubMed]; *An Experimental Electro-Acupuncture Study In Treatment Of The Rat Demyelinated Spinal Cord Injury Induced By Ethidium Bromide*, by Huang S. F., Ding Y, Ruan J. W., Zhang W., Wu J. L., He B., Zhang Y. J., Li Y., Zeng Y. S., published in Neurosci Res. 2011; 70:294-304. [PubMed]; and *Effect Of Epidural Stimulation Of The Lumbosacral Spinal Cord On Voluntary Movement, Standing And Assisted Stepping After Motor Complete Paraplegia: A Case Study*, by Harkema S., Gerasimenko Y., Hodes J., Burdick J., Angeli C., Yangsheng C., Ferreira C., Willhite A., Rejc E., Grossman R. G., and Edgerton V. R., published in Lancet. 2011 337 (9781): 1938-1947.)

Recent work by Xin Geng, et al shows electro acupuncture contributing to a proliferation in neural stem cells, decreasing the levels of inflammatory factors (TNF-α, IL-1α, IL-6 and IL-10), and an inhibition of the Notch signaling pathway normally induced by spinal cord injury, thereby allowing repair of the injured spinal tissue. (See *Electro-acupuncture in the Repair of Spinal Cord Injury: Inhibiting The Notch Signaling Pathway and Promoting Neural Stem Cell Proliferation*, by Xin Geng, Tao Sun, Jing-Hui Li, Ning Zhao, Yong wang, and Hua-Lin Yu, published in Neural Regeneration Research March 2015: 10 (3):394-403.)

However, to date, no focused, integrated system or protocol has been proposed to apply electroacupuncture, or any other art, to a paralysis patient to functionally reverse the paralysis. Various methods and styles of application of electro acupuncture have shown varying degrees of success as documented in the literature, however the literature does not supply a defined protocol for reversing paralysis.

Hence, a need remains in the art for a defined system and method for reversing paralysis.

SUMMARY OF THE INVENTION

The need in the art is addressed by the method and system for applying therapeutic stimulation to a patient stricken with paralysis of the present invention. The inventive method includes the steps of: inserting one or more acupuncture needles against the spine of the patient and applying an electrical potential to the needle with a signal that mimics natural neural impulses in the body. The needle is inserted in parallel with the spinal column against the outermost fleshy layer, behind the bony vertebrae. This allows direct stimulation to penetrate directly through the tissue to the cord itself. The needle is located depending on the nature of the patient's condition. In the illustrative application, the needle is inserted against the Ligamentum flavum, behind the vertebrae of the patient's spine at vertebrae Lumbar 3 (L3). In the best mode, the patient's legs are moved during the application of the electrical potential.

The inventive system is adapted to minimize the Notch reaction at the site of injury by coursing the electricity through the site of injury. This procedure includes an electrode inserted against the Ligamentum flavum of the patient and a circuit for applying an electrical potential to the electrode with a signal that mimics natural neural impulses in the body. In the best mode, the electrode is an acupuncture needle. In the best mode, the acupuncture needles are inserted above and below the injury site, i.e. above and below the L3 vertebrae lumbar. Means are included for moving a limb of the patient during the application of the neural impulses and, in one embodiment, means for adjusting the motor in response to a detection of neural impulses during the application of the signal.

In the illustrative embodiment, the system includes a signal generator, a controller, a motor controller, and a memory in which a program and a database of signal profiles are stored. When executed by the controller, the program applies one or more selected stimulation profiles to the patient through the electrode.

In another embodiment, the system includes an arrangement such as an EEG for detecting and monitoring the patient's neural activity. The program includes code for adjusting the profiles in response to the detected neural activity.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

As noted above, one of the causes of lack of recovery from paralysis has been recognized as a 'notch reaction' that appears to inhibit neurogenesis. See http://www.jneurosci.org/content/32/9/3245.full. Hence, an objective of the invention was to provide a method or system for minimizing the notch reaction at the site of injury in paralysis patients.

As disclosed below, the present invention achieves this objective with a system and method for applying therapeutic stimulation to a patient stricken with paralysis or other conditions. The inventive method (the 'Kelly Protocol') includes the steps of: inserting one or more acupuncture needles against the outer tissue of the spinal column of a patient and applying an electrical potential to the needle with a signal that mimics natural neural impulses in the body. The needles are located depending on the nature of the patient's condition. In the illustrative application, to address leg paralysis, the needles are inserted against the Ligamentum flavum of the patient's spine at the L3 vertebra As discussed more fully below, the needles are inserted above and below the site of injury, at least partially in parallel with the spinal column against the outermost fleshy layer, i.e. the Ligamentum flavum, behind the bony vertebrae. This allows direct stimulation to penetrate directly through the tissue to the cord itself. In the best mode, the patient's legs are moved during the application of the electrical potential.

Figure 1:
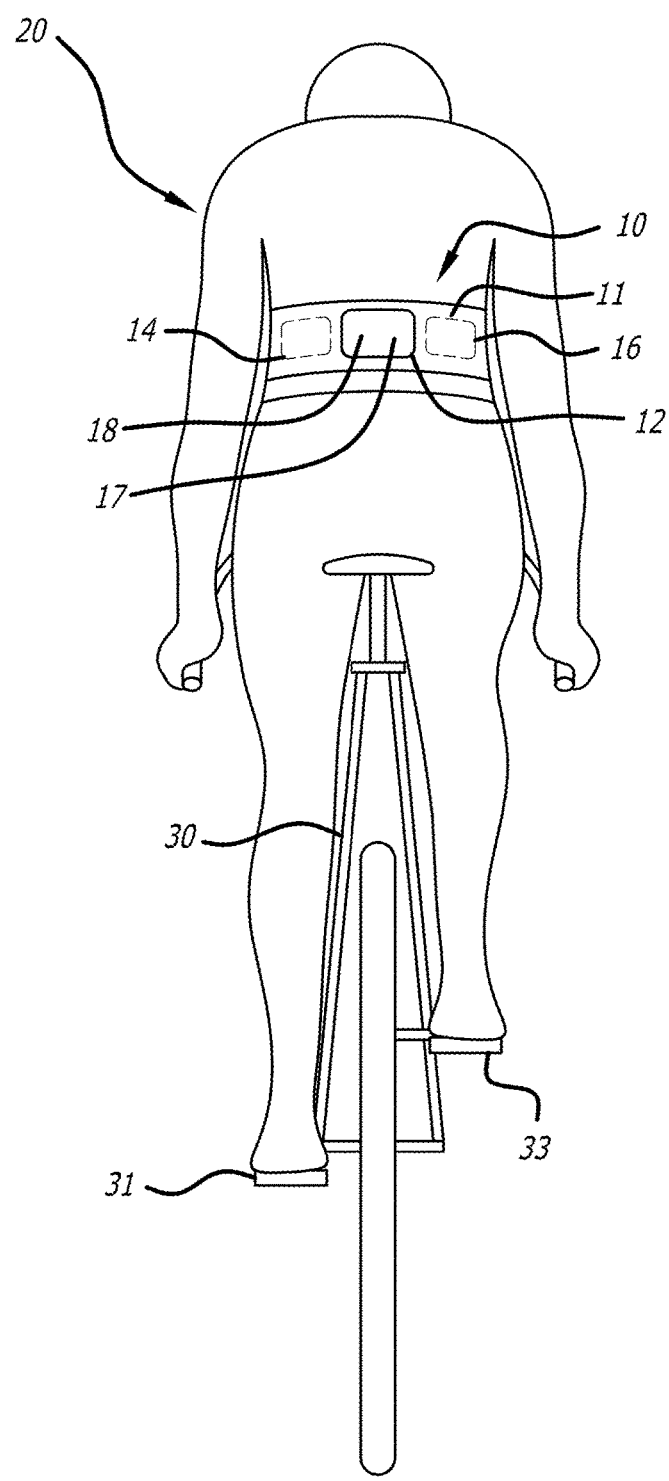
FIG. 1 shows the system of the present invention secured to a patient's body.

An illustrative system for implementing the inventive method is depicted in the figures of which FIG. 1 shows the system 10 (the 'Kelly' stim kit) of the present invention implemented in a belt arrangement. FIG. 1 shows a perspective view of a patient 20 on a stationary bicycle 30 with the acupuncture stim kit 10 installed as a wrap-around belt 11 with an opening 12 therein. The belt 11 may be made of plastic, cloth, rubber or other suitable, preferably at least partially elastic, material. In the best mode, the ends of the belt 11 are secured via a hook and loop type fastener such as Velcro. The opening 12 exposes the back of the patient for insertion of acupuncture needles as discussed more fully below.

Bluetooth enabled electronics 14, in a pocket on one side of the opening 12, provide an electrical signal to an electrode (in the illustrative embodiment: plural acupuncture needles) 17 through a wire connector, e.g., mini alligator clip 18.

The alligator clip is attached at the top of the needle at the handle thereof. The electronics 14 are powered by a battery pack 16 situated in a second pocket. As discussed more fully below, the circuit 14 provides an electrical stimulation profile customized for the user and/or provided by a database (not shown). In addition, the circuit 14 provides controls for a motor (not shown) that moves the patient's limbs during the stimulation session. The circuit 14 and battery pack 16 may be mounted in pockets on or in the belt 11. In FIG. 1, these elements are depicted in phantom to represent mounting within the belt 11.

Those skilled in the art will appreciate that the bicycle 30 may be a recumbent bicycle or other arrangement without departing from the scope of the present teachings. In the best mode, the bicycle 30 is a power assisted pedaler, stationery exercise bike machine pedaling arm exerciser that moves the pedals as the arm bars are moved.

In the illustrative embodiment, the bicycle 30 has pedals 31 and 33, driven by a motor and chain (not shown), into which the patient's feet are clamped. Movement of the limbs (in the illustrative embodiment: the legs) is timed to coincide with the application of the stimulation profile. This movement may be effectuated manually without the motorized bicycle or other mechanism without departing from the scope of the present teachings. This simultaneous application of neural stimulation and coordinated movement was effective in restoring self-controlled movement to a paralysis patient as discussed more fully below. In any case, the key is that the patient be comfortable and that the skin of the patient is exposed to allow for the application of the electrode.

In the illustrative application, the Kelly protocol and system were used to reverse the effects of paralysis in the legs of a patient by inserting the needle(s) 17 against the Ligamentum flavum of a user above and below the L3 vertebra followed by the rest of the needling protocol. However, the invention is not limited thereto.

Figure 2A:
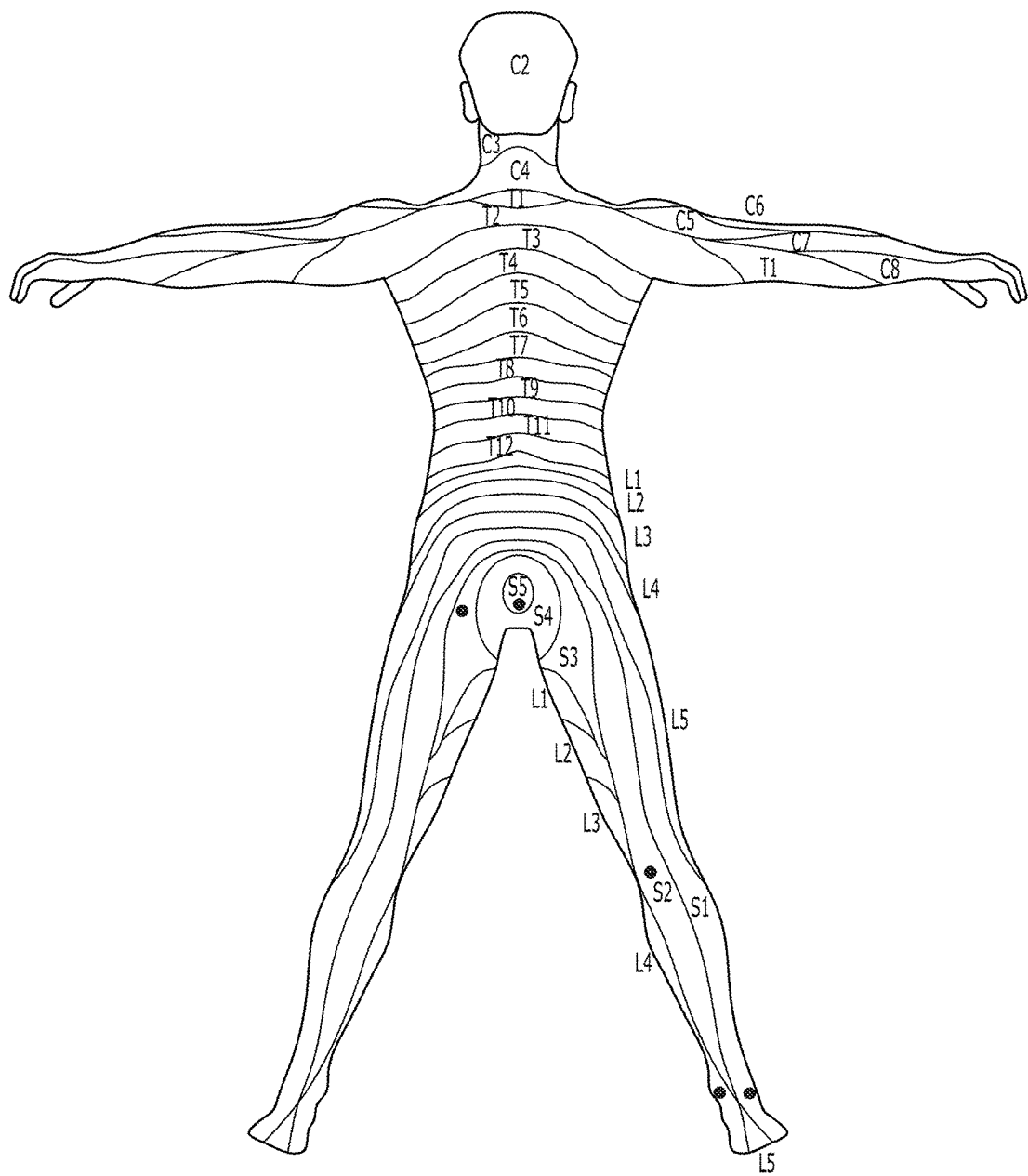
FIG. 2a is an anatomical diagram showing candidate locations along a spine for the application of the system and method of the present invention.

FIG. 2a is an anatomical diagram showing candidate locations along a spine for the application of the system and method of the present invention, including the innervation from the brain through the spinal cord.

Figure 2B:
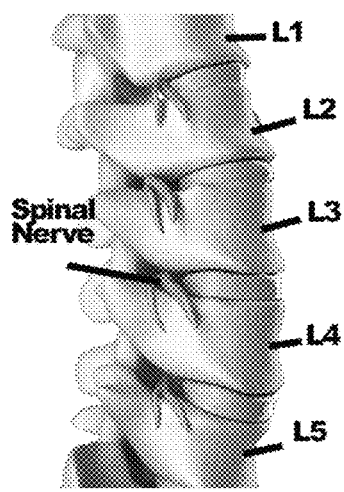
FIG. 2b is a magnified fragmented view of a section of a spine.

FIG. 2b is a magnified fragmented view of a section of a spine.

Figure 2C:
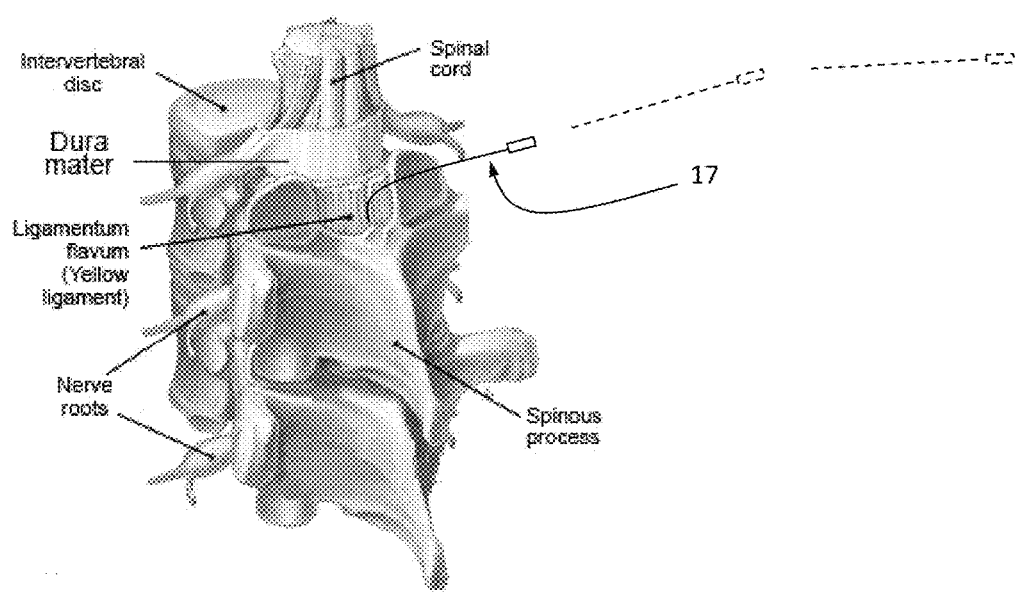
FIG. 2c is a further magnified fragmented view of the spinal section, depicted in FIG. 2b, showing a needle insertion in the Ligamentum flavum in accordance with the present teachings.

FIG. 2c is a further magnified fragmented view of the spinal section, depicted in FIG. 2b, showing an insertion path, in phantom, culminating in a needle insertion at least partially in parallel with the spinal column against the outermost fleshy ligament layer, i.e. the Ligamentum flavum, behind the bony vertebrae in accordance with the Kelly protocol of the present invention. This is achieved by first locating the spinus process to be worked around and inserting the needle in perpendicular in the space between the two spinus processes. The needle is inserted approximately one-quarter to one half inches pass the bony area (vertebra) and then angle it down for another 2-2.5 inches. This should contribute substantially to an induction of current flow in the spinal column substantially greater than that resulting from simply touching this area with the tip of the needle. This allows direct stimulation to penetrate directly through the tissue to the cord itself. This process has been shown to lead to enhanced tissue healing with respect to the notch reaction as mentioned above.

Figure 3:
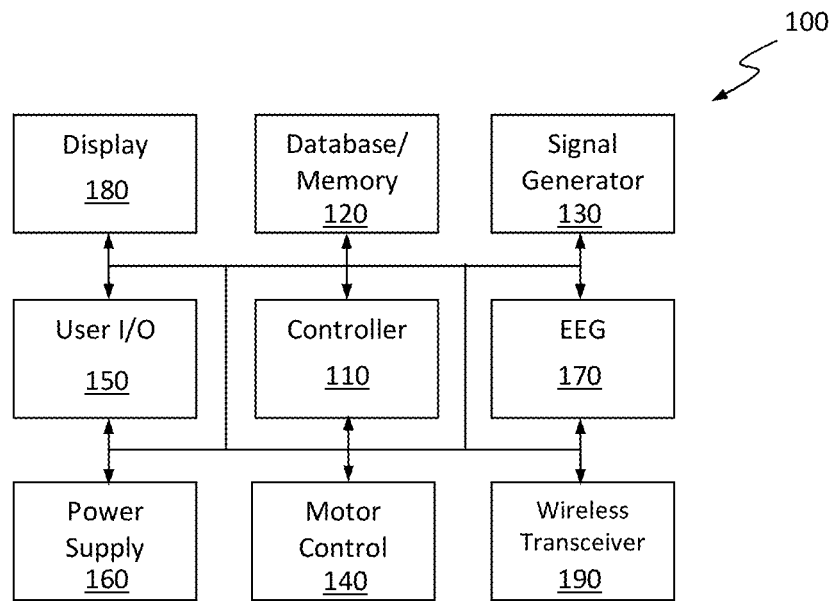
FIG. 3 is a block diagram of an illustrative embodiment of the control system of the present invention.

FIG. 3 is a block diagram of an illustrative embodiment of the control system of the present invention. As shown in FIG. 3, the system 100 includes a controller 110, a database and/or memory 120, a signal generator 130, a motor controller 140, a user interface 150, power supply 160 and electroencephalogram (EEG) 170, display 180 and wireless (e.g. Bluetooth) transceiver 190. The memory stores the software program 200 depicted in FIG. 4 below along with a database of stimulation signal profiles. The stimulation profiles set forth the voltage and/or current levels, duration, frequency and/or waveform of the signal applied to the electrode. The profiles may be preset, supplemented with downloaded data and/or customized by the therapist using the user interface 150.

Select elements, with the exception of the power supply 160, the EEG 170, and display 180 may be implemented in the electronic circuit 14 of FIG. 1. The power supply 160 may be implemented in the battery pack 16 of FIG. 1. Many of the elements depicted in FIG. 3 can be implemented in a standalone system, to which the system 100 is coupled, via a direct or wireless connection, such as a smartphone, tablet, laptop or desktop computer, by way of example.

In one embodiment, the EEG is used to detect and monitor the patient's neural activity. In this case, the program includes code for adjusting the profiles in response to the detected neural activity. The operation of the software is depicted more fully below.

Figure 4:
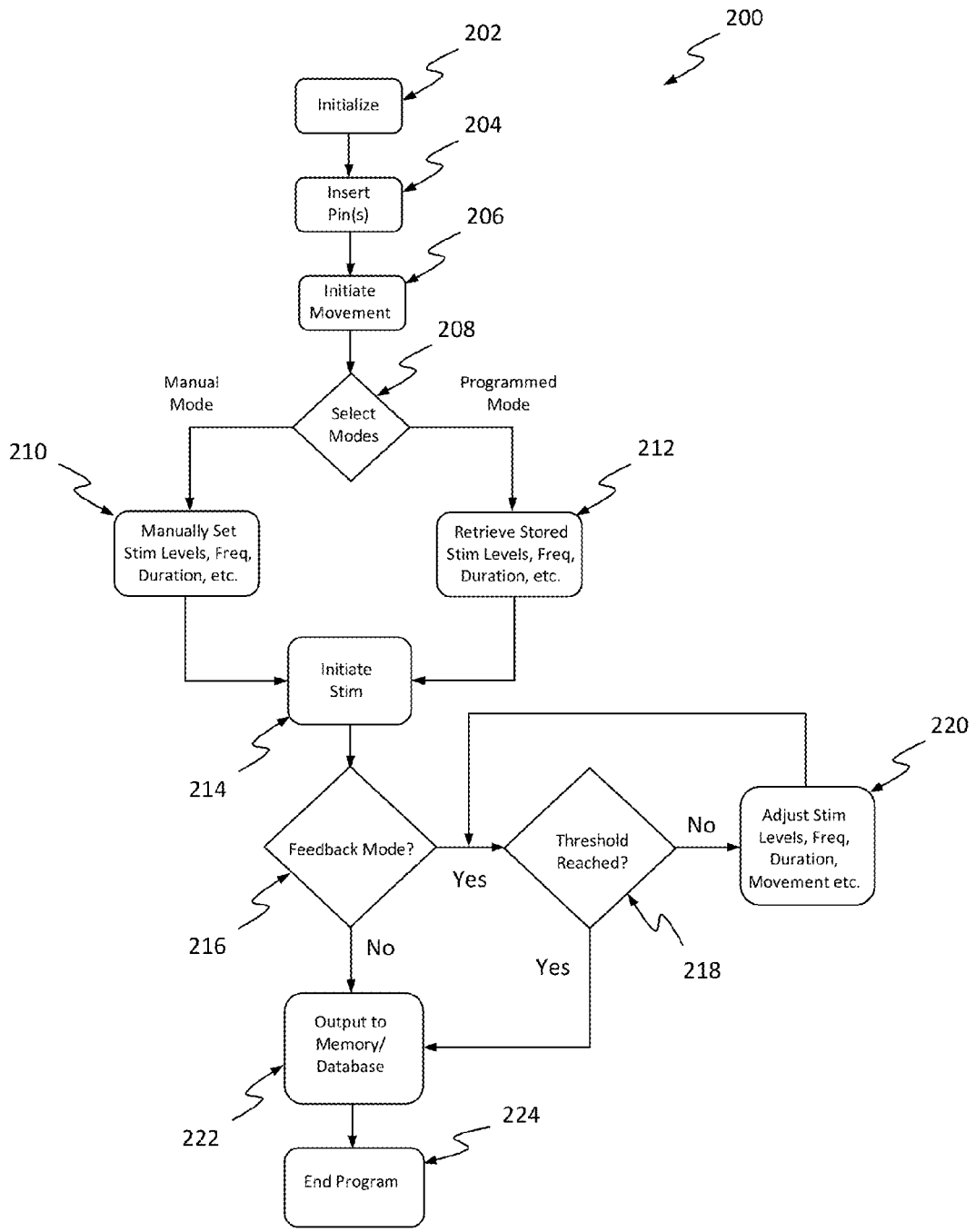
FIG. 4 is a flow diagram of the program executed by the controller depicted in the system of FIG. 4 in accordance with the present teachings.

FIG. 4 is a flow diagram of the program executed by the controller depicted in the system of FIG. 3 in accordance with the present teachings. As is known in the art, the software is stored on a tangible medium and executed by a processor in the controller 110 or external system (not shown).

This software flow diagram depicted in FIG. 4 is a flow diagram depicting the operation of the software executed by the controller 110 of FIG. 3. As shown in FIG. 4, the system 10 initializes at step 202. At step 204 the needle 17 is inserted in the appropriate location. At step 206, movement is initiated. Next, at step 208, mode is selected. If 'manual mode' is selected, then at step 210 the therapist sets stim levels, frequency, duration, etc. If 'programmed mode' is selected, then at step 212 the controller 110 retrieves stored profiles for application. At step 214, stimulation is initiated in accordance with the selected profile.

At step 216, the system checks to see if feedback mode is selected. If no, it outputs data to memory. If yes, then at step 218 the system tests to see if a neural threshold has been reached. If not, then, at step 220, the stim levels are adjusted and tested again against the threshold. This loop repeats until the threshold is met or exceeded at step 218 at which time the system outputs data to memory at step 222. The program then ends at step 224.

Hence the software is stored on a tangible medium and includes code, which when executed by a processor in the controller 110 allows for customizing stimulation for a given user, getting feedback from the user's electrical system as to user's natural nerve voltage levels, using averages stored in a database of users, saving the user's stim sessions and program for each session, providing a schedule for next session, selecting electrodes to stimulated either individually or in simultaneously, recording signal programs used and to be used, controlling and coordinating movement, displaying results obtained with each variant of stim signals applied, and displaying graphical data showing results over time for each stim program. This in-built "learning" system will allow further specificity and usefulness the more the method is applied.

Application:

The Kelly protocol described herein was applied to a 33-year old male with incomplete transection of the spinal cord at approximately C7. He was classified "B" according to ASIA scale. The patient fractured C7 diving into swimming pool on Jun. 26, 2010. He was wired by his surgeon at C6 and C7 to T1 for stability. The surgical scar was to T7. On palpation there did not appear to be anything unusual below T1. He came to the practitioners' office on Jul. 26, 2010, after leaving the hospital, and was treated three (3) times a week for approximately six (6) months. He was receiving no additional treatments.

On his first visit, the patient had vague sensation in his arms but was unable to grasp or use his arms, though he did have some gross motor control of his upper arms, consistent with the lesion site. He had no sensation in the abdominal area though reported vague sensation in his lower legs. He had no sensation or muscular control below the waist, including bladder (he was catheterized), bowel or erectile.

The patient appeared to have bilateral lower motor neuron paralysis, bilateral loss of abdominal and cremaster reflexes, and bilateral loss of tactile discrimination, vibratory and proprioception sensations below the waist.

Traditional acupuncture and customized herbal formulas were started immediately. An experimental treatment strategy was designed and implemented in the last week of August 2010 that included acupuncture, electrical stimulation, and movement of the paralyzed limbs on a stationary bicycle. These treatments were divided into two parts. Part 1 took place on the stationary bicycle; part 2 took place on a treatment table. The table treatments were aimed at improving motor control of the patient's arms and on overall wellness. The bicycle treatments were aimed at facilitating movement to the point that he might become ambulatory.

The stationary bicycle was adapted to allow for access to his spine while seated. Additionally, firm straps were attached to the pedals.

The treatment strategy was based on the concept of bi-directional information flow in conjunction with coursing electrical stimulation through the lesion site. While there is ample literature to support the use of acupuncture and electro-acupuncture in the treatment of paralysis, no literature pertaining to the hypothesis regarding the potential impact of bi-directional information was found.

Kelly Protocol

A Pantheon research electrical stimulator was used, at milliamp setting with symmetrical biphasic modified sine waves. The foundational point of electrical stimulation was L3. A 3 cun (approx. 10 cm) acupuncture needle was inserted at L3 and threaded down between the vertebrae and the Ligamentum flavum. (A 'cun' is a traditional unit of length in China, often called the 'Chinese inch'.) In modern China, the cùn is equal to 3⅓ cm, or about 1.312 336 inches. There are 10 cùn in the chǐ or Chinese foot. The cùn is sometimes identified as the distance between the two outer folds in the bent middle finger, and this personal unit (called the "body inch" in English) is still used by traditional acupuncturists. See http://www.unc.edu/~rowlett/units/dictC.html#cubit.) Milliamp-current electricity was applied in random intervals for 20 minutes. This was done while the patient was seated in the adapted exercise bicycle with his feet strapped onto the pedals. The arm levers of the bicycle were then moved by the practitioner to activate the rotation of the pedals causing the legs to move in cycling motion, while the electricity was coursed.

In the next step, the stimulation was coursed through the whole spinal column from below T7 down through the L3 needle. 3 cun needles were placed along the spinal column from below T7 to the needle at L3. The needle at L3 was then connected with electrical wire to 1 cun (approx. 3.33 cm) needles inserted at acupuncture points Gall Bladder meridian 34 (GB 34; in front and below the fibular head in Extensor digitorum longus), Urinary Bladder meridian 57 (UB57; center of the lower cleft of the gastrocnemius) and GB41 (distal to the junction of the bases of the fourth and fifth metatarsals). Random pulse milliamp-current for 20 minutes was applied while the bicycle pedals were activated.

For the first week the basic spinal protocol was followed. Additional points were then alternated. First, a series of points one inch lateral to each spinal process from T7 through L5 (Hua Tuo points) were electrified at every third point. This was done once a week in place of the basic protocol. Additionally, points in the 8 sacral foramen (Bai Liao points) were needled and electrified in the uppermost foramen once every two weeks. These points outside of the direct lesion site were chosen in order to extend the benefits into the environment surrounding the lesion. Studies show that electroacupuncture improves the local microenvironment of the spinal cord and induces tissue antioxidant formation lowering the production of excitatory amino acids, inhibiting apoptosis and necrosis. Leg points on the meridians of the lower legs (GB meridian, Stomach (ST) meridian and UB meridian) were also rotated and electrified at each treatment to stimulate as much of the leg as possible.

When the surgery site was clearly healed at week 2 of treatment, the electrical stimulation was then applied from above the fracture site using 1 cun needles at C6, which were then connected via electrical wire to the spinal needles below T7, to L3 and the sacrum. This created an electrical flow below and above the site of injury, potentially creating an inhibition of the Notch reaction at the site of injury, theoretically then clearing the way for healing of the neural tissue.

RESULTS

By Sep. 9, 2010, approximately two weeks into the experimental protocol significant improvements were observed. As of that date the patient had regained full use of his arms and hands, full control of his bladder and urinary function, had full sensation of his bowel but not enough strength to push, and erectile function. He had gained control of his abdominal muscles as well as abdominal sensation. He was able to balance sitting up without using his arms to hold himself up. He was able to do a push-up and stomach crunches. Sensation in his legs had increased. His appetite was good and he did not appear to have any other residual trauma. He expressed the desire and stamina to heal, and started on an exercise regimen of push-ups and stomach crunches daily.

At this point the experimental protocol was continued for an additional 8 weeks. At week 5, movement was observed in the patient's toes. Improvement continued until gross motor control returned to his toes, then his legs. Customized herbal formulas were continuous throughout the treatment. At the end of his treatment period of six months in January 2011, the patient was walking on his own with the use of a 3-sided walker.

Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A system for restoring motor control of a patient including:
   an elongate acupuncture needle adapted for nonsurgical transcutaneous insertion into a spinal cavity of the patient whereby a portion of said needle is internal to the patient's body at least partially in parallel with and against the dura and ligament tissue and against one of the dura and ligament tissue of the patient's spine in the epidural space in a spinous process to repair spinal cord transection and restore muscle control and a portion of the needle is external to the patient's body;
   a circuit for applying an electrical potential to the external portion of the needle with a signal that mimics natural neural impulses in the patient's body in order to transmit and signals along the spinal column to restore movement; and
   means including a motor for moving a limb of the patient during the application of the signal.

2. The invention of claim 1 further including means for adjusting the motor in response to a detection of neural impulses during the application of the signal.

3. The invention of claim 1 wherein the system includes a memory.

4. The invention of claim 3 wherein the memory stores a database of signal profiles.

5. The invention of claim 3 wherein the memory includes a program which when executed by the controller applies one or more selected stimulation profiles to a patient through the needle.

6. The invention of claim 5 wherein the program stores data relating to a patient's therapy sessions with respect to the profiles.

7. The invention of claim 6 further including means for detecting and monitoring the patient's neural activity.

8. The invention of claim 7 wherein the program includes code for adjusting the profiles in response to the detected neural activity.

9. The invention of claim 1 wherein the system includes an electroencephalogram.

10. A system for applying therapeutic stimulation to a patient stricken with paralysis including:
    an elongate flexible acupuncture needle adapted for nonsurgical transcutaneous insertion into a spinal cavity of the patient whereby a portion of said needle is internal to the patient's body at least partially in parallel with and against the dura and ligament tissue and against one of the dura and ligament tissue of the patient's spine in the epidural space in a spinous process to repair spinal cord transection and restore muscle control;
    a system for applying an electrical potential to a portion of the needle external to the patient's body with a signal that mimics natural neural impulses in the patient's body in order to transmit said signals along the spinal column to restore movement;
    means for moving a limb of the body during the application of the neural impulses, said means for moving including a motor and means for adjusting the motor in response to a detection of neural impulses during the application of the signal;
    means for detecting the patient's neural activity during the application of the signal; and
    means for changing the stimulation profile in response to the means for detecting the patient's neural activity.

11. The invention of claim 10 wherein the needle is inserted into the epidural space of the patient's spine at L3.

12. A nonsurgical method for applying therapeutic stimulation to a patient including the steps of:
nonsurgically inserting an elongate flexible needle into a spinal cavity of the patient whereby a portion of said needle is internal to the patient's body at least partially in parallel with and against dura and ligament tissue and against one of the dura and ligament tissue of the patient's spine in the epidural space in a spinous process to repair spinal cord transection and restore muscle control and a portion of the needle is external to the patient's body and
applying an electrical potential to the external portion of the needle with a signal that mimics natural neural impulses in the patient's body in order to transmit said signals along the spinal column to restore movement.

13. The invention of claim 12 wherein the needle is inserted against the ligamentum flavum of the patient's spine at L3.

14. The invention of claim 13 further including the step of moving the legs of the patient during the application of the electrical potential.

* * * * *